(12) United States Patent
Liang et al.

(10) Patent No.: US 11,134,723 B2
(45) Date of Patent: Oct. 5, 2021

(54) FAR-INFRARED FIBERS, AND COMPONENTS AND USES OF THE SAME

(71) Applicant: Green Energy Nano Technology Co., Ltd., Taipei (TW)

(72) Inventors: Tien-Show Liang, Taipei (TW); En Meng, Taipei (TW); Shou-Hung Tang, Taipei (TW); Juin-Hong Cherng, Taipei (TW)

(73) Assignee: GREEN ENERGY NANO TECHNOLOGY CO., LTD., Taipei (TW)

( * ) Notice: Subject to any disclaimer, the term of this patent is extended or adjusted under 35 U.S.C. 154(b) by 423 days.

(21) Appl. No.: 16/136,141

(22) Filed: Sep. 19, 2018

(65) Prior Publication Data

US 2019/0082747 A1    Mar. 21, 2019

(30) Foreign Application Priority Data

Sep. 20, 2017   (TW) .................. 106132199

(51) Int. Cl.
*A41B 17/00* (2006.01)
*A61F 5/41* (2006.01)
(Continued)

(52) U.S. Cl.
CPC ............... *A41B 17/00* (2013.01); *A41B 9/02* (2013.01); *A61F 5/41* (2013.01); *C08J 3/226* (2013.01);
(Continued)

(58) Field of Classification Search
CPC ....... A41B 9/02; A41B 17/00; A41B 2300/00; A41B 9/00; A61F 5/41; D01F 1/106; D01F 6/04; D01F 6/06

USPC ..... 442/181; 428/357, 364, 34.1, 35.7, 35.8, 428/36.1, 365, 373, 397, 398, 402; 264/165, 176.1; 2/400
See application file for complete search history.

(56) References Cited

U.S. PATENT DOCUMENTS 7,147,874 B2    12/2006   Kang et al.
8,211,006 B2     7/2012   Park
(Continued)

FOREIGN PATENT DOCUMENTS

CN    101929019 A    12/2010
CN    102302224 A     1/2012
(Continued)

OTHER PUBLICATIONS

Japanese Office Action dated Nov. 5, 2019.
(Continued)

*Primary Examiner* — Matthew D Matzek
(74) *Attorney, Agent, or Firm* — Michael W. Ferrell; Ferrells, PLLC; Anna L. Kinney

(57) ABSTRACT

Far-infrared fibers, and components and uses of the same are provided. The far-infrared fibers can be used together with other optional fibers to provide a product containing far-infrared fibers. The product does not emit harmful radiation and could raise a user's body temperature safely to increase the volume and rate of the user's blood flow without affecting the blood pressure and pulse of the user. Furthermore, the product can be male underpants that can improve male sexual function without affecting the physiological state.

14 Claims, 14 Drawing Sheets

(51) Int. Cl.
   *D01F 1/10*   (2006.01)
   *D01D 5/24*   (2006.01)
   *D01D 5/34*   (2006.01)
   *C08J 3/22*   (2006.01)
   *D01F 6/04*   (2006.01)
   *D01F 6/06*   (2006.01)
   *A41B 9/02*   (2006.01)

(52) U.S. Cl.
   CPC ............... *D01D 5/24* (2013.01); *D01D 5/34* (2013.01); *D01F 1/106* (2013.01); *D01F 6/04* (2013.01); *D01F 6/06* (2013.01); *C08J 2367/02* (2013.01); *C08J 2467/02* (2013.01)

(56) References Cited

U.S. PATENT DOCUMENTS

| | | | | |
|---|---|---|---|---|
| 10,470,509 | B1* | 11/2019 | Knott | ............ A41D 31/04 |
| 2013/0341819 | A1* | 12/2013 | Liang | ............ A47G 9/007 |
| | | | | 264/103 |
| 2014/0212662 | A1 | 7/2014 | Weng | |
| 2015/0346402 | A1 | 12/2015 | Kao et al. | |

FOREIGN PATENT DOCUMENTS

| | | |
|---|---|---|
| CN | 103504885 A | 1/2014 |
| CN | 105131586 A | 12/2015 |
| CN | 205585328 U | 9/2016 |
| EP | 262147 A2 | 8/2013 |
| JP | S6392720 A | 4/1988 |
| JP | H02259110 A | 10/1990 |
| JP | 2003082524 A | 3/2003 |
| TW | 200628645 A | 8/2006 |
| TW | 201641755 A | 12/2016 |
| WO | 2012042446 A2 | 4/2012 |

OTHER PUBLICATIONS

Taiwanese Office Action with Search Report dated May 31, 2019.
Chinese Office Action dated Dec. 9, 2020.
Official Notification of Office Action/Search Report issued by the Patent Office of Gulf Cooperation Council (GCCPO) dated Feb. 21, 2021, with Search Report.

* cited by examiner

| International Index of Erectile Function-5 items (IIEF-5) | | |
|---|---|---|
| Over the past 6 months: | | |
| 1. | How do you rate your confidence that you could get and keep an erection? | |
| | ☐ No confidence (0) ☐ Very low (1)<br>☐ Low (2) ☐ Moderate (3)<br>☐ High (4) ☐ Very high (5) | |
| 2. | When you had erections with sexual stimulation, how often were your erections hard enough for penetration? | |
| | ☐ No sexuality (0) ☐ Always (5)<br>☐ Most times (4) ☐ Sometimes (3)<br>☐ A few times (2) ☐ Never (1) | |
| 3. | During sexual intercourse, how often were you able to maintain your erection after you had penetrated your partner? | |
| | ☐ No sexuality (0) ☐ Always (5)<br>☐ Most times (4) ☐ Sometimes (3)<br>☐ A few times (2) ☐ Never (1) | |
| 4. | During sexual intercourse, how difficult was it to maintain your erection to completion of intercourse? | |
| | ☐ No sexuality (0) ☐ Always (5)<br>☐ Most times (4) ☐ Sometimes (3)<br>☐ A few times (2) ☐ Never (1) | |
| 5. | When you attempted sexual intercourse, how often was it satisfactory for you? | |
| | ☐ No sexuality (0) ☐ Always (5)<br>☐ Most times (4) ☐ Sometimes (3)<br>☐ A few times (2) ☐ Never (1) | |
| | Total score | |

FIG. 3

| | Validation of Portuguese version of Quality of Erection Questionnaire (QEQ) |
|---|---|
| 1. | You had erections hard enough for penetration of your partner:<br><br>☐Always (5) ☐Most times (4)<br>☐Sometimes (3) ☐A few times (2)<br>☐Never (1) |
| 2. | Your ability to keep your erection to completion of sexual intercourse was:<br><br>☐Very satisfactory (5)<br>☐Neither satisfactory ☐Somewhat satisfactory (4)<br>    nor unsatisfactory (3) ☐Somewhat unsatisfactory (2)<br>☐Very unsatisfactory (1) |
| 3. | The length of time (from when you started sexual activity) until your erection was hard enough to participate in sexual intercourse was:<br><br>☐Very satisfactory (5)<br>☐Neither satisfactory ☐Somewhat satisfactory (4)<br>    nor unsatisfactory (3) ☐Somewhat unsatisfactory (2)<br>☐Very unsatisfactory (1) |
| 4. | The hardness of your erection was:<br><br>☐Very satisfactory (5)<br>☐Neither satisfactory ☐Somewhat satisfactory (4)<br>    nor unsatisfactory (3) ☐Somewhat unsatisfactory (2)<br>☐Very unsatisfactory (1) |
| 5. | The overall quality of your erection was:<br><br>☐Very satisfactory (5)<br>☐Neither satisfactory ☐Somewhat satisfactory (4)<br>    nor unsatisfactory (3) ☐Somewhat unsatisfactory (2)<br>☐Very unsatisfactory (1) |
| | Total score |

FIG. 4

| Premature Ejaculation Diagnostic Tool (PEDT) | | | | |
|---|---|---|---|---|
| 1. | How difficult is it for you to delay ejaculation? | | | |
| | ☐Not difficult at all<br>☐Moderately difficult<br>☐Extremely difficult | (0)<br>(2)<br>(4) | ☐Somewhat difficult<br>☐Very difficult | (1)<br>(3) |
| 2. | Do you ejaculate before you want to? | | | |
| | ☐Never or almost never (0%)<br>☐About half the time (50%)<br>☐Always or almost always (100%) | (0)<br>(2)<br>(4) | ☐Less than half the time (25%)<br>☐Over half the time (75%) | (1)<br>(3) |
| 3. | Do you ejaculate with very little stimulation? | | | |
| | ☐Never or almost never (0%)<br>☐About half the time (50%)<br>☐Always or almost always (100%) | (0)<br>(2)<br>(4) | ☐Less than half the time (25%)<br>☐Over half the time (75%) | (1)<br>(3) |
| 4. | Do you feel frustrated because of ejaculating before you want to? | | | |
| | ☐Not at all<br>☐Moderately<br>☐Extremely | (0)<br>(2)<br>(4) | ☐Slightly<br>☐Very | (1)<br>(3) |
| 5. | How concerned are you that your time to ejaculation leaves your partner unfulfilled? | | | |
| | ☐Not at all<br>☐Moderately<br>☐Extremely | (0)<br>(2)<br>(4) | ☐Slightly<br>☐Very | (1)<br>(3) |
| | | | Total score | |

FIG. 5

| International Prostate Symptom Score (IPSS) | |
|---|---|
| 1. | Incomplete emptying: In the past month, how often have you had the sensation of not emptying your bladder? <br> ☐ Not at all (0)  ☐ Less than 1 in 5 times (1) <br> ☐ Less than half the time (2)  ☐ About half the time (3) <br> ☐ More than half the time (4)  ☐ Almost always (5) |
| 2. | Frequency: In the past month, how often have you had to urinate less than every two hours? <br> ☐ Not at all (0)  ☐ Less than 1 in 5 times (1) <br> ☐ Less than half the time (2)  ☐ About half the time (3) <br> ☐ More than half the time (4)  ☐ Almost always (5) |
| 3. | Intermittency: In the past month, how often have you found you stopped and started again several times when you urination? <br> ☐ Not at all (0)  ☐ Less than 1 in 5 times (1) <br> ☐ Less than half the time (2)  ☐ About half the time (3) <br> ☐ More than half the time (4)  ☐ Almost always (5) |
| 4. | Urgency: In the past month, how often have you found it difficult to postpone urination? <br> ☐ Not at all (0)  ☐ Less than 1 in 5 times (1) <br> ☐ Less than half the time (2)  ☐ About half the time (3) <br> ☐ More than half the time (4)  ☐ Almost always (5) |
| 5. | Weak stream: In the past month, how often have you had a weak urinary stream? <br> ☐ Not at all (0)  ☐ Less than 1 in 5 times (1) <br> ☐ Less than half the time (2)  ☐ About half the time (3) <br> ☐ More than half the time (4)  ☐ Almost always (5) |
| 6. | Straining: In the past month, how often have you had to strain to start urination? <br> ☐ Not at all (0)  ☐ Less than 1 in 5 times (1) <br> ☐ Less than half the time (2)  ☐ About half the time (3) <br> ☐ More than half the time (4)  ☐ Almost always (5) |
| 7. | Nocturia: In the past month, how many times did you typically get up at night to urinate? <br> ☐ None (0)  ☐ Once (1) <br> ☐ Twice (2)  ☐ Thrice (3) <br> ☐ 4 times (4)  ☐ More than 5 times (5) |
| | Total score |

FIG. 6

FAR-INFRARED FIBERS, AND COMPONENTS AND USES OF THE SAME

CLAIM FOR PRIORITY

This application claims the benefit of Taiwan Patent Application No. 106132199, filed on Sep. 20, 2017, the subject matters of which are incorporated herein by reference.

FIELD OF THE INVENTION

The present invention relates to a far-infrared fiber and components and uses of the same. Specifically, the present invention relates to a masterbatch for manufacturing far-infrared fibers, far-infrared fibers manufactured thereby and products of the far-infrared fibers. The far-infrared fibers are especially useful for manufacturing underpants that can improve male sexual function.

BACKGROUND OF THE INVENTION

Male sexual dysfunctions can be generally divided into erectile dysfunction (ED), premature ejaculation (PE), delayed ejaculation, and low libido. Factors causing male sexual dysfunction can be divided into mental, physiological or drug factors. Mental factors include depression, low self-confidence, and anxiety over sexual performance. Physiological factors include injury of the penile cavernosum, endocrine system diseases, and cardiovascular diseases. Drug factors include side effects induced by hypertension and psychiatric drugs.

Clinical data shows that about 50% of all males over the age of 50 are facing erectile problems, e.g., erectile dysfunction (ED) or premature ejaculation (PE), and therefore cannot have normal sexual intercourse. In clinical practice, these problems are usually solved by drugs such as an oral phosphodiesterase-5 (PDE5) inhibitor which is highly tolerant and convenient. Examples of the phosphodiesterase-5 inhibitor include Viagra® (sildenafil), Levitra® (vardenafil) and Cialis® (tadalafil). However, phosphodiesterase-5 inhibitors are not suitable for patients with cardiac disease (e.g., patients suffering from angina pectoris, heart failure, and heart-related diseases), stroke, or sickle-cell disease because the interaction between phosphodiesterase-5 inhibitors and some drugs may endanger the patients. Phosphodiesterase-5 inhibitors may also cause side effects, such as headache, dizziness, flushed face, stomach discomfort, abnormal visual perception, snuffling, myalgia, backache, etc., to other people.

In view of the side effects of phosphodiesterase-5 inhibitors, U.S. Pat. No. 7,147,874 discloses a pharmaceutical composition for preventing and treating premature ejaculation. The pharmaceutical composition comprises an extract of *Bufonis Venenum* and an extract of *Ginseng* with saponins. The pharmaceutical composition can be applied to a male's glans to provide the effect of extending sexual intercourse by reducing the contraction of penile muscle and providing regional anesthesia. However, the pharmaceutical composition does not really improve male sexual dysfunction but temporarily provides a prevention from premature ejaculation for each sexual intercourse. Furthermore, even the pharmaceutical composition consists of herbal extracts; whether it will adversely affect users' bodies after long-term use is unknown.

U.S. Pat. No. 8,211,006 discloses a male erection stabilizer. Instead of using drugs such as Viagra, Levitra, Cialis or the herbal composition to treat male sexual dysfunction, the male erection stabilizer physically improves penile erection via a special mechanism. However, the male erection stabilizer is put on the user's penis and therefore might cause injury to the penis if used frequently.

The aforementioned known therapies for improving male sexual dysfunction, no matter pharmacotherapies or physiotherapy using an assistive device, all have a risk of jeopardizing the user's health.

SUMMARY OF THE INVENTION

In view of the above technical problem, the present invention provides a far-infrared fiber and its products. Examples of products include but are not limited to daily necessities such as sleeping accommodation, underwear, and underpants. The products of the far-infrared fiber of the present invention do not emit harmful radiation and could raise a user's body temperature safely to increase the volume and rate of the user's blood flow without affecting the blood pressure and pulse of the user. Furthermore, the underpants manufactured by the far-infrared fiber can improve male sexual function without affecting the physiological state. The objectives of the present invention will be explained below.

An objective of the present invention is to provide a masterbatch for manufacturing far-infrared fibers, comprising:

a first polymer matrix; and a first far-infrared filler dispersed in the first polymer matrix, wherein the first far-infrared filler contains the following elements: titanium (Ti), germanium (Ge), zinc (Zn), aluminum (Al), and magnesium (Mg), and wherein the first far-infrared filler does not contain the following elements: scandium (Sc), vanadium (V), chromium (Cr), cobalt (Co), and antimony (Sb).

In some embodiments of the present invention, the first far-infrared filler further contains elements selected from the following group: silicon (Si), copper (Cu), calcium (Ca), iron (Fe), barium (Ba), potassium (K), sodium (Na), and compositions thereof. In the preferred embodiments of the present invention, the first far-infrared filler further contains the following elements: silicon, copper, calcium, iron, barium, potassium, and sodium.

In some embodiments of the present invention, the first far-infrared filler further contains the elements selected from the following group: manganese (Mn), nickel (Ni), gallium (Ga), and compositions thereof.

In some embodiments of the present invention, based on the total weight of the masterbatch, the amount of titanium ranges from 5 wt % to 40 wt %, the amount of germanium ranges from 0.01 wt % to 1 wt %, the amount of zinc ranges from 1 wt % to 12 wt %, the amount of aluminum ranges from 3 wt % to 16 wt %, and the amount of magnesium ranges from 1 wt % to 15 wt %.

In some embodiments of the present invention, the first polymer matrix is selected from the following group: polyester, polyurethane (PU), poly(vinyl chloride) (PVC), polypropylene (PP), polyamide (PA), and polyethylenimine (PEI).

Another objective of the present invention is to provide a far-infrared fiber, which is manufactured by using the aforementioned masterbatch and a second polymer.

In some embodiments of the present invention, the far-infrared fiber is a core-shell fiber, which has a core layer and a shell layer coating the core layer along the long-axis direction of the far-infrared fiber, and wherein the core layer is manufactured by using the masterbatch and the second polymer and the shell layer is formed by a third polymer. The shell layer of the far-infrared fiber may further contain a second far-infrared filler dispersed in the third polymer, wherein the second far-infrared filler contains the following elements: titanium, germanium, zinc, aluminum, and magnesium, and does not contain the following elements: scandium, vanadium, chromium, cobalt, and antimony.

In some embodiments of the present invention, the second polymer and the third polymer are respectively selected from the following group: polyester, polyurethane, poly (vinyl chloride), poly propylene, polyamide, and silicone. Silicone is the preferred option.

In some embodiments of the present invention, the far-infrared fiber is a hollow fiber.

Still another objective of the present invention is to provide a product of far-infrared fiber, which is manufactured by the aforesaid far-infrared fibers and other optional fibers.

In some embodiments of the present invention, the far-infrared fibers further comprise metal granules that adhere to the surface of the far-infrared fiber, wherein the metal granules are the granules of metal selected from the following group: gold (Au), platinum (Pt), and a composition thereof.

In some embodiments of the present invention, the product is underpants, wherein the proportion of the far-infrared fibers in the part of the underpants that corresponds to the front side of the user's pelvis is 40% or more based on the total number of the far-infrared fibers and other optional fibers in that part.

Still another objective of the present invention is to provide a method for manufacturing underpants useful in improving male sexual function. The method comprises steps of using the aforesaid far-infrared fiber and other optional fibers to manufacture the underpants, wherein the proportion of the far-infrared fibers in the part of the underpants that corresponds to the front side of the user's pelvis is 40% or more based on the total number of the far-infrared fibers and other optional fibers in that part.

To render the above objectives, technical features, and advantages of the present invention more apparent, the present invention will be described in detail with reference to some embodiments hereinafter.

BRIEF DESCRIPTION OF THE DRAWINGS

FIG. 3 shows the International Index of Erectile Function-5 items (also called as "IIEF-5") used herein.

FIG. 4 shows the Validation of Portuguese version of Quality of Erection Questionnaire (also called as "QEQ") used herein.

FIG. 5 shows the Premature Ejaculation Diagnostic Tool (also called as "PEDT") used herein.

FIG. 6 shows the International Prostate Symptom Score (also called as "IPSS") used herein.

In FIGS. 7 to 14, the subjects of the "Control group" wore normal commercial underpants, while the subjects of the "Experimental group" wore underpants manufactured by using the far-infrared fibers of the present invention. In FIGS. 8, 10, 12 and 14, "Period 1" compares the scores after two months of testing to the scores after one month of testing, "Period 2" compares the scores after three months of testing to the scores after two months of testing, and "Period 3" compares the scores after three months of testing to the scores after one month of testing.

DESCRIPTION OF THE PREFERRED EMBODIMENT

Figure 1A:
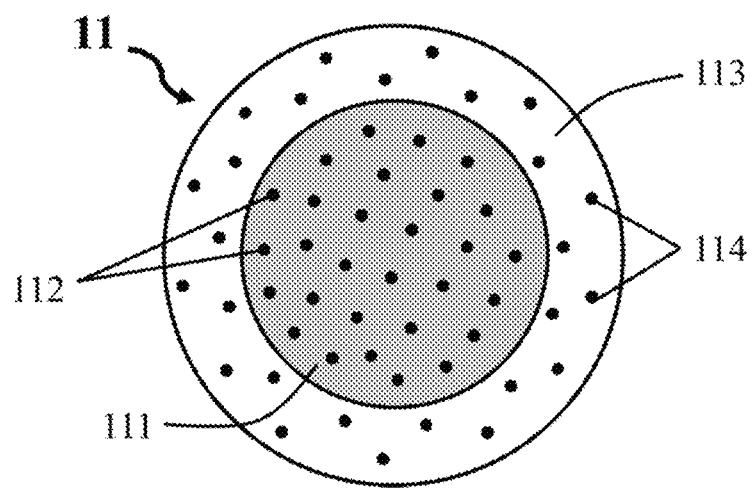
FIG. 1a schematically shows a cross section of a far-infrared fiber according to an embodiment of the present invention, wherein the cross section is perpendicular to the long-axis of the far-infrared fiber.

The following paragraphs will describe some of the embodiments of the present invention in detail. However, without departing from the spirit of the present invention, the present invention may be embodied in various embodiments and should not be limited to the specific embodiments described in the specification.

Unless it is additionally explained, the expression "a," "an," "the," or the like recited in the specification (especially in the claims) should include both the singular and plural forms.

As used herein, the terms such as "first", "second", "third" or the like are used to distinguish different elements, components, areas, layers, and/or sections, not terms supplying a numerical limit.

1. Masterbatch for Manufacturing Far-Infrared Fibers

The present invention provides a masterbatch (also called as "far-infrared masterbatch") for manufacturing fibers that can emit a far-infrared ray (also called as "far-infrared fibers"). The master batch comprises a first polymer matrix and a first far-infrared filler dispersed in the first polymer matrix. The first far-infrared filler contains titanium (Ti), germanium (Ge), zinc (Zn), aluminum (Al), and magnesium (Mg), and does not contain any of scandium (Sc), vanadium (V), chromium (Cr), cobalt (Co), and antimony (Sb). It is found through experiments that the first far-infrared filler with the above elementary composition can emit a far-infrared ray with a wavelength perfectly suitable for humans, i.e., a wavelength ranging from 2 μm to 22 μm, especially from 4 μm to 14 μm. In particular, the first far-infrared filler can emit a far-infrared ray with a wavelength ranging from 6 μm to 6.5 μm. Furthermore, as proved by the experimental results provided in the appended examples, the first far-infrared filler can raise a user's body temperature safely to increase the volume and rate of the user's blood flow and enhance male sexual function without affecting the blood pressure and pulse of the user.

The first far-infrared filler may further comprise other elements that can emit a far-infrared ray. In some embodiments of the present invention, the first far-infrared filler further comprise elements selected from the following group: silicon (Si), copper (Cu), calcium (Ca), iron (Fe), barium (Ba), potassium (K), sodium (Na), and compositions thereof. Without departing from the objectives of the present invention, the first far-infrared filler may also comprise elements not mentioned above but capable of emitting a far-infrared ray, such as manganese (Mn), nickel (Ni) and gallium (Ga). In a specific embodiment of the present invention, the first far-infrared filler further comprises silicon, copper, calcium, iron, barium, potassium and sodium.

The elements contained in the first far-infrared filler can be provided in various forms such as in the form of their compounds containing oxygen, carbon, oxygen and carbon, or an amino group, but the present invention is not limited thereto. Based on the disclosure of the specification, persons having ordinary skills in the art choose one or more suitable compounds containing oxygen, carbon, oxygen and carbon or an amino group to provide the first far-infrared filler with the desired elementary composition.

In the far-infrared masterbatch of the present invention, the amount of the first far-infrared filler could be optionally adjusted. To provide sufficient and stable far-infrared rays based on the total weight of the far-infrared masterbatch, the amount of titanium preferably ranges from 5 wt % to 40 wt %, the amount of germanium preferably ranges from 0.01 wt % to 1 wt %, the amount of zinc preferably ranges from 1 wt % to 12 wt %, the amount of aluminum preferably ranges from 3 wt % to 16 wt %, and the amount of magnesium preferably ranges from 1 wt % to 15 wt %. If silicon is used, the amount of silicon in the first far-infrared filler preferably ranges from 12 wt % to 22 wt %. In some embodiments of the present invention, based on the total weight of the far-infrared masterbatch, the amounts of titanium, germanium, zinc, aluminum and magnesium in the first far-infrared filler are as follows: the amount of titanium ranges from 11 wt % to 18 wt %, such as 12 wt %, 13 wt %, 14 wt %, 15 wt %, 16 wt %, or 17 wt %; the amount of germanium ranges from 0.05 wt % to 0.5 wt %, such as 0.1 wt %, 0.15 wt %, 0.2 wt %, 0.25 wt %, 0.3 wt %, or 0.4 wt %; the amount of zinc ranges from 1 wt % to 12 wt %, such as 2 wt %, 3 wt %, 4 wt %, 5 wt %, 6 wt %, 7 wt %, 8 wt %, 9 wt %, 10 wt %, or 11 wt %; the amount of aluminum ranges from 3 wt % to 16 wt %, such as 4 wt %, 5 wt %, 6 wt %, 7 wt %, 8 wt %, 9 wt %, 10 wt %, or 11 wt %; and the amount of magnesium ranges from 1 wt % to 15 wt %, such as 2 wt %, 3 wt %, 4 wt %, 5 wt %, 6 wt %, 7 wt %, 8 wt %, 9 wt %, 10 wt %, 11 wt %, 12 wt %, or 13 wt %.

Examples of the first polymer matrix of far-infrared masterbatch according to the present invention include: polyester, polyurethane (PU), poly(vinyl chloride) (PVC), poly propylene (PP), polyamide (PA), and amino group-containing polymers (e.g., polyethylenimine (PEI)). In some embodiments of the present invention, the first polymer matrix is polyethylene terephthalate (PET), polybutylene terephthalate (PBT), or a combination thereof. For example, in a specific embodiment of the present invention, the first polymer matrix is polybutylene terephthalate (PBT).

The manufacturing method of the far-infrared masterbatch of the present invention is not particularly limited and can be any conventional method known to persons skilled in the art. For example, the far-infrared masterbatch can be prepared by mixing the first far-infrared filler, the first polymer matrix and a dispersant with a high-speed mixer to obtain a homogeneous mixture of the first far-infrared filler, the first polymer matrix and dispersant and then extruding the homogeneous mixture at a high temperature by using an extruder.

2. Far-Infrared Fibers

The far-infrared masterbatch of the present invention can be used together with other polymer(s) to manufacture far-infrared fibers. Therefore, the present invention also provides a far-infrared fiber, which is manufactured by using the far-infrared masterbatch of the present invention and a second polymer. As used herein, a far-infrared fiber refers to a fiber that can emit a far-infrared ray.

The manufacturing method of the far-infrared fiber is not particularly limited and can be any conventional method, such as a full granulation method, masterbatch method, and injection method. However, the masterbatch method is preferred. Using the masterbatch method for example, the far-infrared fibers can be manufactured by blending the far-infrared masterbatches and the second polymer in a predetermined weight ratio, such as 1:9, 2:8, 3:7, 7:13, 2:3, or 1:1, to obtain a blend, and spinning the blend at a high temperature (depending on the polymer) to obtain the far-infrared fibers. The temperature of the spinning procedure is not particularly limited, as long as the fluidity of the first and second polymer matrix is sufficient that the first far-infrared fillers can be uniformly dispersed therein.

In the preferred embodiment of the present invention, the far-infrared fiber is a core-shell fiber. As schematically shown in FIG. 1a, the far-infrared fiber 11 has a core layer 111, which is manufactured from the far-infrared masterbatch and the second polymer, and a shell layer 113 coating the core layer 111 along the long-axis direction of the far-infrared fiber, wherein the core layer 111 contains uniformly dispersed first far-infrared fillers 112. The shell layer 113 is formed of a third polymer, and optionally, may further contains second far-infrared fillers 114 dispersed therein. In the specification, the second far-infrared fillers 114 has the same definition as the first far-infrared filler 112 and can be identical to or different from the first far-infrared fillers 112.

The second polymer and third polymer can be identical to or different from each other and can be selected from the following group: polyester, polyurethane (PU), poly(vinyl chloride) (PVC), poly propylene (PP), polyamide (PA), and silicone. Examples of polyester include polyethylene terephthalate (PET), polybutylene terephthalate (PBT) and a combination thereof. In view of the research that some polymers, like the polymers prepared using monomers containing vinyl groups, may cause symptoms such as skin flushing or itching to infants or patients with sensitive skin, silicone is the preferred third polymer. An example of silicone is that contains 50 wt % of silica and has a polymerized unit of $[Si(CH_3)_2O]_n$, wherein n is an integer from 50 to 100.

The shape of the far-infrared fiber of the present invention is not particularly limited. For example, the cross section perpendicular to the long-axis of the far-infrared fiber can be circular, elliptic, triangular, quadrangular or other polygonal, X-shaped, Y-shaped, or cross-shaped. But the present invention is not limited thereto.

Figure 1B:
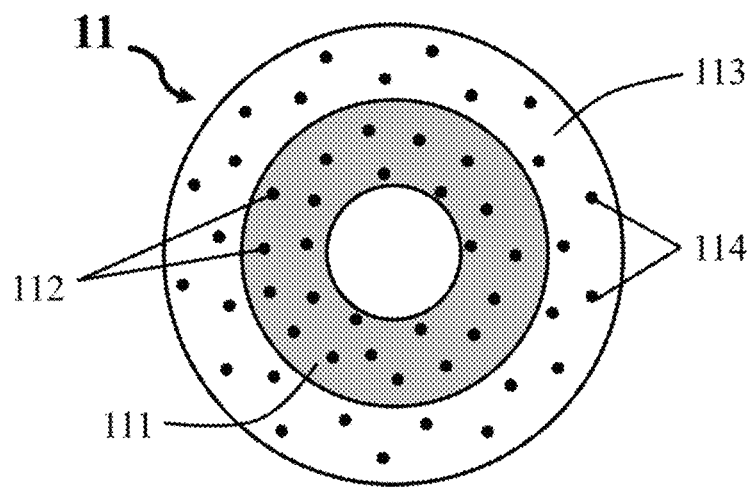
FIG. 1b schematically shows a cross section of a far-infrared fiber according to another embodiment of the present invention, wherein the cross section is perpendicular to the long-axis of the far-infrared fiber.

In some preferred embodiments of the present invention, as schematically shown in FIG. 1b, the far-infrared fiber is hollow so that it is lightweight and more elastic.

3. Products of Far-Infrared Fibers

The far-infrared fibers of the present invention, alone or together with other fibers, could be used to manufacture various products that can emit a far-infrared ray. Therefore, the present invention also provides a product of far-infrared fibers, which is manufactured by the far-infrared fibers of the present invention and other optional fibers. Examples of the product include but are not limited to sleeping accommodation (e.g., a blanket, a bed mat, a bed sheet, etc.), clothes (tops, pants, underpants, etc.), a chair cushion, an eye mask, a waist belt, a neck guard, an elbow guard, a shawl, and a topical patch.

In some embodiments of the present invention, the product of far-infrared fibers can be a blanket or clothes, which could raise a user's body temperature safely to increase the volume and rate of the user's blood flow without affecting the blood pressure and pulse of the user.

Figure 2A:
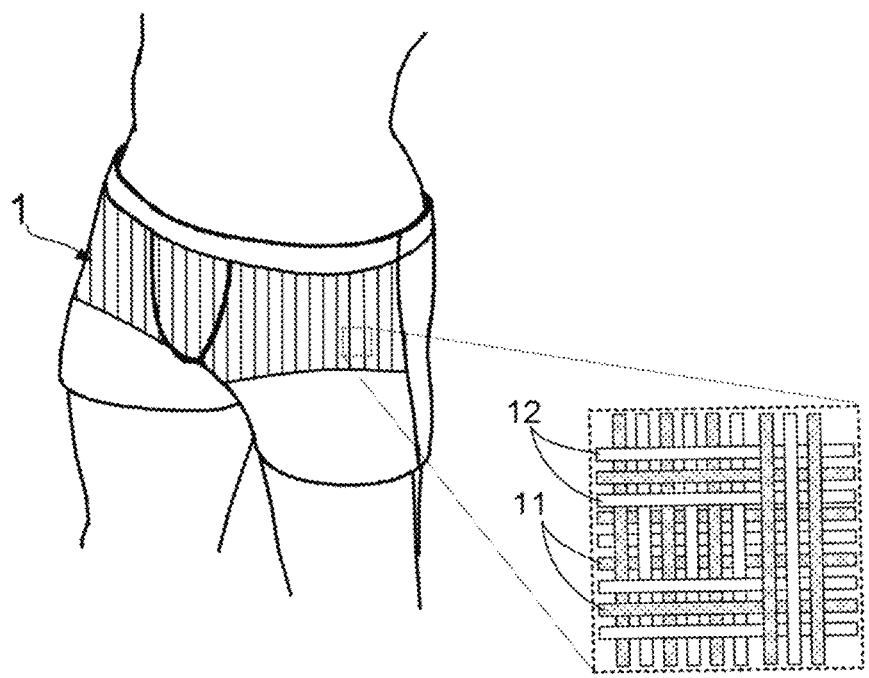
FIG. 2a schematically shows an embodiment of underpants manufactured by using the far-infrared fibers of the present invention.

In the preferred embodiments of the present invention, the products of the far-infrared fibers are male underpants that can improve male sexual function without affecting the physiological state of the user. To provide the above effect, the male underpants must be made with the proviso that if only a portion of the fibers in the male underpants is the far-infrared fiber of the present invention, as shown in FIG. 2a, the proportion of the far-infrared fibers 11 in the part of the underpants 1 that corresponds to the front side of a male user's pelvis must be 40% or more based on the total number of the far-infrared fibers 11 and other fibers 12.

In some embodiments of the present invention, the products of far-infrared fiber may further comprise metal selected from the following group: gold (Au), platinum (Pt), and a combination thereof.

4. Methods for Manufacturing Underpants Useful in Improving Male Sexual Function As described above, the underpants manufactured by using the far-infrared fiber of the present invention can improve male sexual function without affecting the physiological state of the user. Therefore, the present invention also provides a method for manufacturing underpants useful in improving male sexual function, wherein the underpants are manufactured by using the far-infrared fibers of the present invention and other optional fibers. It is preferred that the proportion of the far-infrared fibers in the part of the underpants that corresponds to the front side of a user's pelvis is 40% or more based on the total number of the far-infrared fibers and other optional fibers in that part.

5. Examples

5.1. Preparation of Masterbatches for Manufacturing Far-Infrared Fibers

The first far-infrared filler, a dispersant, and polyethylene terephthalate (PET) (the first polymer matrix) were evenly mixed by a mixer, wherein the first far-infrared filler included the following elements: titanium, germanium, zinc, aluminum, magnesium, silicon, copper, calcium, iron, barium, potassium, and sodium. The obtained mixture of the first far-infrared filler, dispersant, first polymer matrix were extruded by an extruder at a temperature ranging from 248 to 255□ to obtain the masterbatches for manufacturing far-infrared fibers.

5.2. Preparation of Far-Infrared Fibers

The obtained masterbatches and polybutylene terephthalate (PBT) were blended in a weight ratio of 35:65 to obtain a blend. The blend was extruded by an extruder at a temperature of 263□, and subjected to procedures including a screw spinning, winding, and post-process, to obtain a far-infrared fiber, wherein the far-infrared fiber was a hollow fiber as shown in FIG. 1b.

5.3. Example 1: Blanket with Function of Emitting a Far-Infrared Ray

5.3.1. Preparation Method

The far-infrared fibers and normal fibers were knitted into a blanket with the function of emitting a far-infrared ray (also called as "far-infrared blanket") by using a knitting machine, wherein the proportion of far-infrared fibers was 45 to 48% based on the total number of the fibers of the blanket.

5.3.2. Test of Capability in Enhancing Human Blood Circulation 5.3.2.1. Testing Method:

(1) Subject: a 23 years-old man wearing a short sleeve top and trousers during the test;

(2) Experimental environment: an environmental temperature of 18±1□ and a relative humidity of 50±2%;

(3) Testing position: the abdomen, waist and shoulder of the subject;

(4) Testing apparatus: Laser Doppler Blood Flow Monitor (Moor instrument; Model No.: moorVMS-LDF);

(5) Adaptive period: the subject was allowed to lie down without the cover of the far-infrared blanket for 20 minutes, and then the volume of blood flow, rate of blood flow and skin temperature of the subject were measured and recorded in Table 1; and (6) Testing period: the subject was allowed to lie down with the cover of the far-infrared blanket for 30 minutes, and then the volume of blood flow, rate of blood flow and skin temperature of the subject were measured and recorded in Table 1.

TABLE 1

| Tested items | | Testing results | | |
| --- | --- | --- | --- | --- |
| | | Abdomen | Waist | Shoulder |
| Volume of blood flow | Adaptive period | 36.6 | 60.0 | 37.9 |
| | Testing period | 54.3 | 73.0 | 49.0 |
| | Rate of change (%) | 48.5 | 21.7 | 29.3 |
| Rate of blood flow | Adaptive period | 9.0 | 12.0 | 7.8 |
| | Testing period | 13.5 | 14.0 | 8.8 |
| | Rate of change (%) | 50.0 | 16.7 | 12.9 |
| Skin temperature (□) | Adaptive period | 31.3 | 31.2 | 31.4 |
| | Testing period | 33.3 | 32.6 | 33.5 |
| | Rate of change (%) | 2.0 | 1.4 | 2.1 |

5.3.2.2. Experimental Analysis:

As can be seen from Table 1, the volume and rate of blood flow of the subject were significantly increased after being covered with the far-infrared blanket while the skin temperature of the subject was not changed significantly but only increased slightly. The results show that the products of the far-infrared fibers of the present invention can effectively enhance human blood circulation under the premises that the user's body surface temperature is increased safely and the blood pressure and pulse of the user is maintained normally.

Figure 2B:
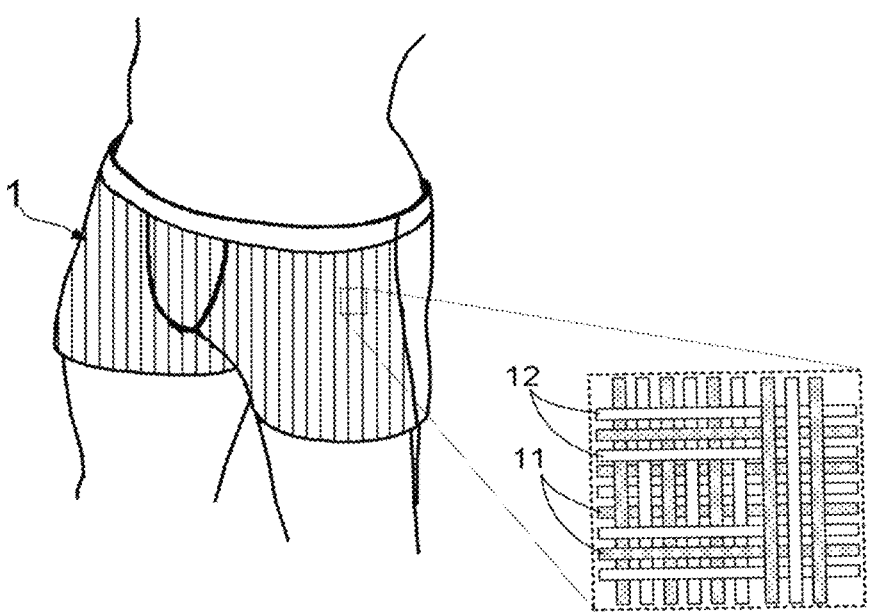
FIG. 2b schematically shows another embodiment of underpants manufactured by using the far-infrared fibers of the present invention.

5.4. Example 2: Underpants with Function of Emitting a Far-Infrared Ray 5.4.1. Preparation Method The far-infrared fibers and cotton fibers were knitted into underpants with the function of emitting a far-infrared ray (also called as "far-infrared underpants") as shown in FIG. 2b by using a knitting machine, wherein the far-infrared fibers were only presented in the front panel of underpants, and the proportion of the far-infrared fibers was 48% based on the total number of the far-infrared fibers and cotton fibers.

5.4.2. Analysis of Harmful Radiation

The far-infrared underpants were subjected to a gamma-spectrometric analysis conducted by the Environmental Media Radioanalytical Laboratory, Institute of Nuclear Energy Research, Atomic Energy council, Executive Yuan. The results show that there was no detectable thorium-series, uranium-series, potassium-40 nuclear species, or other artificial gamma-radiation nuclear species, wherein the detection limit of the instrument to thorium-series, uranium-series and potassium-40 nuclear species is 0.044 Bq/g, 0.031 Bq/g and 0.216 Bq/g, respectively. That is, the far-infrared product of the present invention will not cause any radiation relevant adverse effects.

5.4.3. Capability Test 5.4.3.1. Qualifications of Subjects

To reduce interference factors, the following subjects were excluded from this test:

(1) a subject who was subjected to a therapy of penile cavernosum via oral drugs (Sildenafil Vardenafil or Tadalafil), a drug injection, a vacuum aspirator within 7 days prior to this test;

(2) a subject who takes antihypertensive drugs (doxazosin or nitrate), antidepressants, sedatives, hormone preparation (anti-androgen), or drugs for treating peptic ulcer (cimetidine) for a long period of time;

(3) a subject suffering from serious injuries of the central system such as a stroke or spinal cord injury within 6 months prior to this test;

(4) a subject suffering from male sexual dysfunction because of non-vascular factors such as nervous factors or hormone factors;

(5) a subject suffering from vascular sclerosis;

(6) a subject suffering from psychologically induced male sexual dysfunction;

(7) a subject who has been subjected to a complete resection of prostate gland or a resection of prostatic urethra;

(8) a subject suffering from HIV or liver diseases;

(9) a subject with abnormal genitalia or suffering from a disease making him avoid sexual intercourse;

(10) a subject with a sexual partner who is pregnant or lactating;

(11) a subject suffering from Peyronie's disease;

(12) a subject suffering from alcoholism or tobacco addiction;

(13) a subject suffering from malignant tumors or prostate cancer;

(14) a subject that is subjected to a surgery during this test; and

(15) a subject with a serious clinical or mental condition that may interfere with the experimental procedure or evaluation during this test.

5.4.3.2. Testing Method

To understand the capability of the far-infrared fibers of the present invention in improving male sexual function, the inventors of the present invention separated 28 subjects into two clusters on the basis of whether the subject was diagnosed as having male sexual dysfunction, and randomly divided the subjects in each cluster into a control group and an experimental group for a three-month clinical test. During the test, each of the subjects wore the far-infrared underpants of the present invention (experimental group) or commercial underpants (control group), and was subjected to several tests for evaluating male sexual function every month. Also, the physiological data of each subject was measured every month to confirm the physiological state of each subject.

Tables 2 and 3 show the result of the physiological test, average age and BMI calculation of the subjects diagnosed or not diagnosed with male sexual dysfunction prior to the test, wherein the abnormal subjects in each group are subjects with hypertension.

TABLE 2

| | Physiological test | | Ages (years-old) | | | BMI | | |
| --- | --- | --- | --- | --- | --- | --- | --- | --- |
| | Normal | Abnormal | Average | ± | Variation | Normal | Overweight | Obesity |
| Control group (n = 5) | 4 | 1 | 46.66 | ± | 5.36 | 2 | 3 | 0 |
| Experimental group (n = 14) | 13 | 1 | 48.93 | ± | 7.45 | 2 | 8 | 4 |

TABLE 3

| Physiological test | Ages (years-old) | | | | BMI | | |
|---|---|---|---|---|---|---|---|
| | Normal | Abnormal | Average | ± | Variation | Normal | Overweight | Obesity |
| Control group (n = 4) | 3 | 1 | 49 | ± | 8.18 | 2 | 2 | 0 |
| Experimental group (n = 5) | 4 | 1 | 47 | ± | 6.45 | 2 | 3 | 0 |

5.4.3.3. Analysis of Physiological Data

To check the health state of each subject during the test, the subjects were subjected to a physiological test including systolic blood pressure (SBP), diastolic blood pressure (DBP), body temperature and pulse prior to the test and every month during the test. The related results of physiological test are shown in Tables 4 to 7, wherein Table 4 shows the results of physiological test prior to the test, Table 5 shows the results of physiological test after one month of testing, Table 6 shows the results of physiological test after two months of testing, and Table 7 shows the results of physiological test after three months of testing.

TABLE 4

Results of physiological test prior to testing
Prior to testing

| Physiological data | Average value | ± | Variation | Maximum | Minimum |
|---|---|---|---|---|---|
| SBP (mmHg) | 132.57 | ± | 11.11 | 153.00 | 114.00 |
| DBP (mmHg) | 86.79 | ± | 10.30 | 105.00 | 71.00 |
| Body temperature (° C.) | 36.53 | ± | 0.27 | 36.80 | 36.00 |
| Pulse (bit/min) | 72.07 | ± | 6.18 | 84.00 | 59.00 |

TABLE 5

Results of physiological test after one month of testing
After one month of testing

| Physiological data | Average value | ± | Variation | Maximum | Minimum |
|---|---|---|---|---|---|
| SBP (mmHg) | 126.64 | ± | 9.92 | 147.00 | 108.00 |
| DBP (mmHg) | 80.86 | ± | 9.13 | 98.00 | 64.00 |
| Body temperature (° C.) | 36.37 | ± | 0.56 | 37.2 | 35.00 |
| Pulse (bit/min) | 73.29 | ± | 7.25 | 93.00 | 64.00 |

TABLE 6

Results of physiological test after two months of testing
After two months of testing

| Physiological data | Average value | ± | Variation | Maximum | Minimum |
|---|---|---|---|---|---|
| SBP (mmHg) | 123.33 | ± | 8.50 | 140.00 | 110.00 |
| DBP (mmHg) | 83.44 | ± | 6.64 | 92.00 | 71.00 |
| Body temperature (° C.) | 36.64 | ± | 0.29 | 37.00 | 36.20 |
| Pulse (bit/min) | 74.44 | ± | 8.23 | 96.00 | 64.00 |

TABLE 7

Results of physiological test after three months of test
After three months of testing

| Physiological data | Average value | ± | Variation | Maximum | Minimum |
|---|---|---|---|---|---|
| SBP (mmHg) | 126.00 | ± | 8.29 | 135.00 | 115.00 |
| DBP (mmHg) | 84.00 | ± | 7.79 | 93.00 | 74.00 |
| Body temperature (° C.) | 36.20 | ± | 0.28 | 36.60 | 36.00 |
| Pulse (bit/min) | 73.67 | ± | 12.12 | 90.00 | 61.00 |

As can be seen from Tables 4 to 7, there is no significant variation in the physiological data of the subjects before and after wearing the far-infrared underpants of the present invention. The results manifest that the far-infrared fiber of the present invention is harmless to user's health and therefore is safe to users.

5.4.3.4. Evaluation of Erectile Function and Quality

In this test, the effects of the far-infrared underpants of the present invention in improving erectile function and quality for subjects diagnosed or not diagnosed with male sexual dysfunction during a three-month test were evaluated by the following questionnaires: the International Index of Erectile Function-5 items (IIEF-5, as shown in FIG. 3) and the Validation of Portuguese version of Quality of Erection Questionnaire (QEQ, as shown in FIG. 4). The higher the scores of the two questionnaires the better the erectile function and quality.

Figure 7:
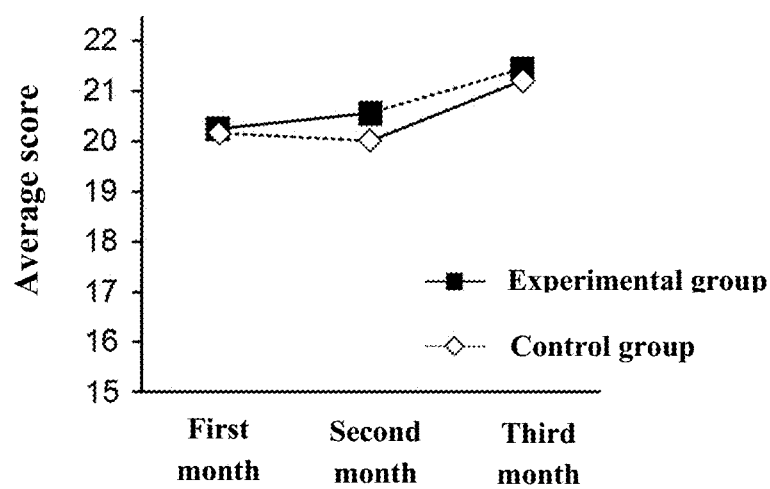
FIG. 7 to FIG. 14 show the results of the clinical test for evaluating the effects of underpants manufactured by using the far-infrared fibers of the present invention in improving sexual function for the subjects "diagnosed" with male sexual dysfunction, wherein the clinical test was conducted for three months. The average score (FIG. 7) and variation of score (FIG. 8) of IIEF-5, the average score (FIG. 9) and variation of score (FIG. 10) of QEQ, the average score (FIG. 11) and variation of score (FIG. 12) of PEDT, and the average score (FIG. 13) and variation of score (FIG. 14) of IPSS after one month of testing, two months of testing and, three months of testing are provided, respectively.
Figure 8:
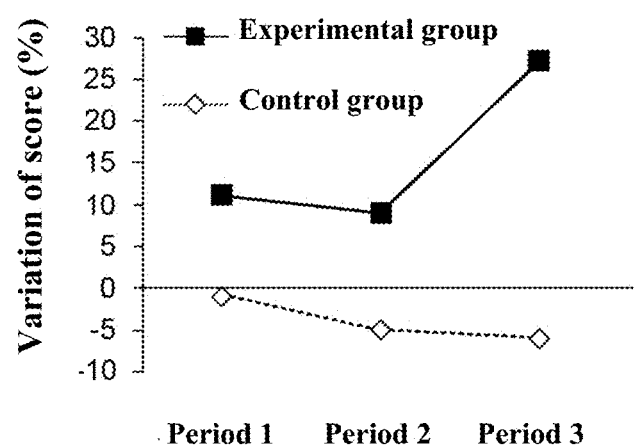
Figure 15:
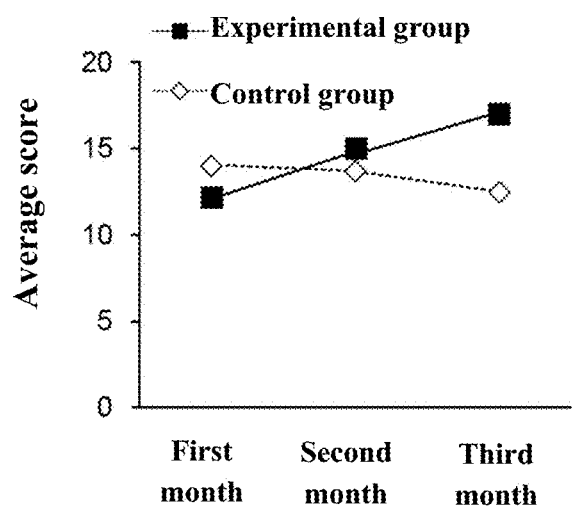
FIGS. 15 to 22 show the results of the clinical test for evaluating the effects of underpants of far-infrared fibers in improving sexual function for the subjects "not diagnosed" with male sexual dysfunction, wherein the clinical test was conducted for three months. The average score (FIG. 15) and variation of score (FIG. 16) of IIEF-5, the average score (FIG. 17) and variation of score (FIG. 18) of QEQ, the average score (FIG. 19) and variation of score (FIG. 20) of PEDT, and the average score (FIG. 21) and variation of score (FIG. 22) of IPSS after one month of testing, two months of testing and, three months of testing are provided, respectively. The definitions of "Control group", "Experimental group", "Period 1", "Period 2" and "Period 3" in FIG. 15 to FIG. 22 are identical to those in FIGS. 7 to 14.
Figure 16:
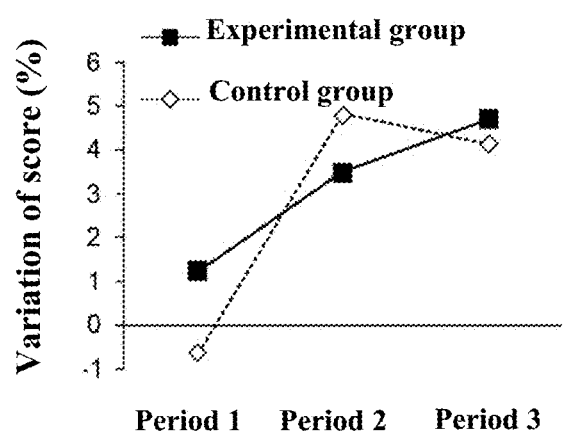

FIGS. 7 and 15 show the average scores of IIEF-5 for subjects diagnosed or not diagnosed with male sexual dysfunction every month during the test, respectively. FIGS. 8 and 16 show the variation in score percentage between two different months, wherein the score percentage was converted from the scores of the control group or experimental group based on the full marks of questionnaires (i.e., the full marks of questionnaire is 100%).

As can be seen from FIGS. 7, 8, 15 and 16, during the three-month testing of wearing the far-infrared underpants of the present invention, the scores of the subjects were generally increased, no matter whether the subject was diagnosed with male sexual dysfunction or not. That is, the far-infrared underpants of the present invention can improve erectile function.

Figure 9:
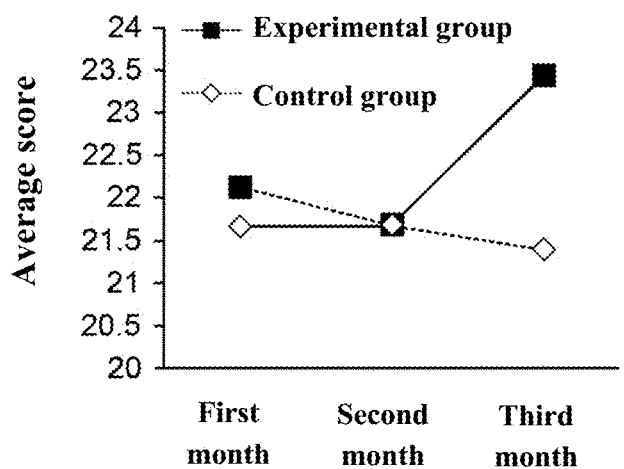
Figure 10:
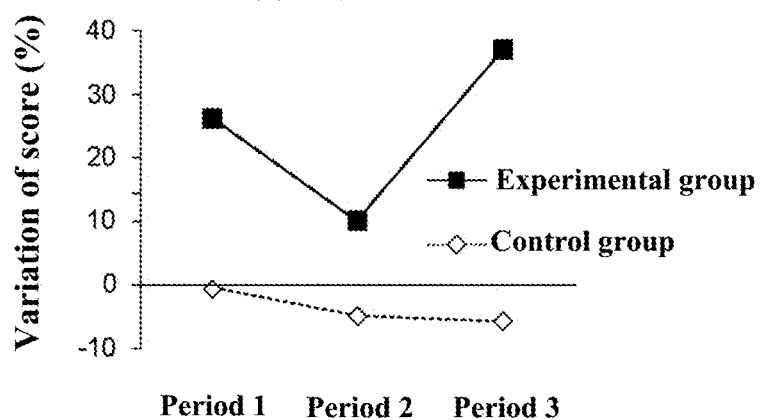
Figure 17:
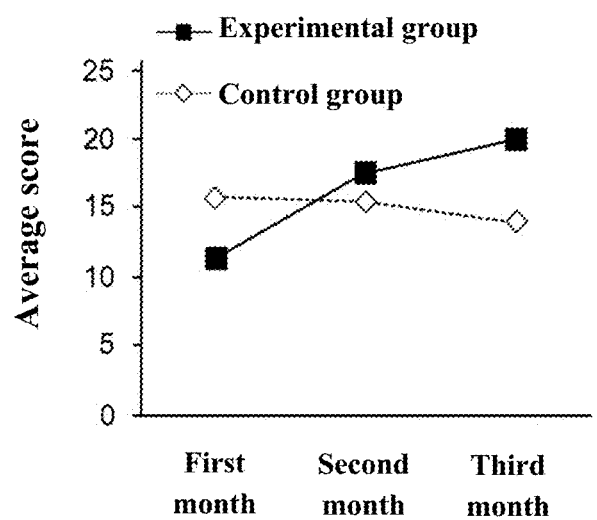
Figure 18:
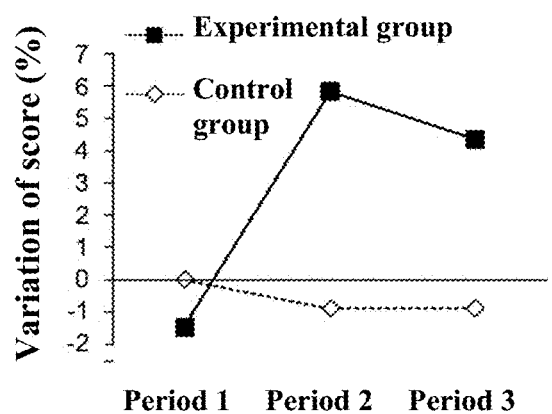

FIGS. 9 and 17 show the average scores of QEQ for subjects diagnosed or not diagnosed with male sexual dysfunction every month during the test, respectively. FIGS. 10 and 18 show the variation in score percentage between two different months, wherein the score percentage was converted from the scores of control group or experimental group based on the full marks of QEQ questionnaire (i.e., the full marks of QEQ questionnaire is 100%).

As can be seen from FIGS. 9, 10, 17 and 18, during the three-month testing of wearing the far-infrared underpants of the present invention, the scores of the subjects were generally increased, no matter whether the subject is diagnosed with male sexual dysfunction or not. That is, the far-infrared underpants of the present invention can improve erectile quality.

5.4.3.5. Evaluation of Capability in Controlling Ejaculation

In this test, the effect of far-infrared underpants of the present invention in improving the ability to control ejaculation for subjects diagnosed or not diagnosed with male sexual dysfunction during three-month test was evaluated by the following questionnaire: the Premature Ejaculation Diagnostic Tool (PEDT, as shown in FIG. 5). The lower the score of the questionnaire the better the ability to control ejaculation.

Figure 11:
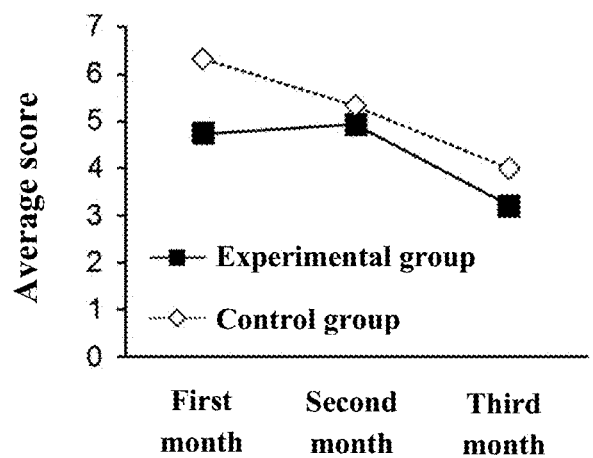
Figure 12:
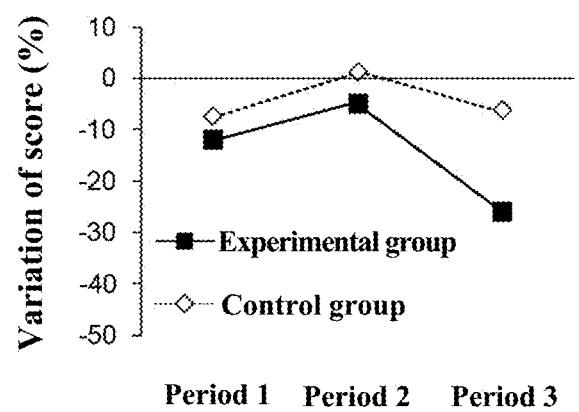
Figure 19:
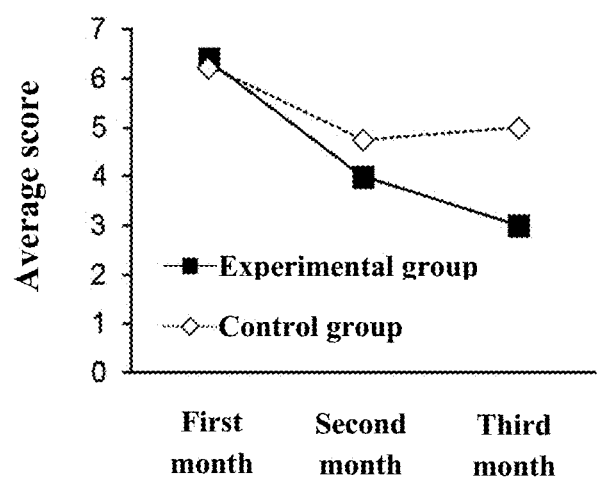
Figure 20:
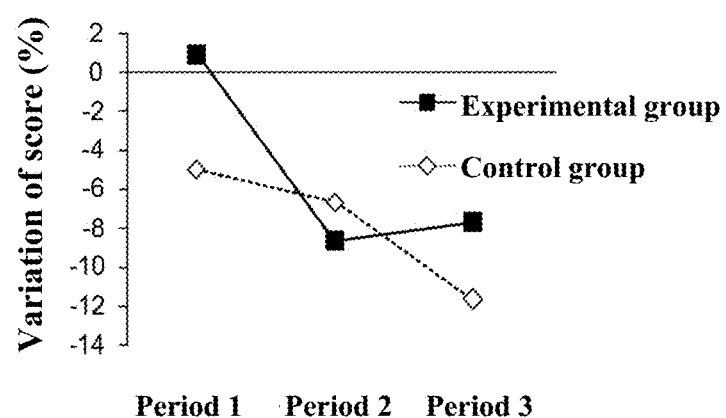

FIGS. 11 and 19 show the average scores of PEDT for subjects diagnosed or not diagnosed with male sexual dysfunction every month during the test, respectively. FIGS. 12 and 20 show the variation in score percentage between two different months, wherein the score percentage was converted from the scores of control group or experimental group based on the full marks of PEDT questionnaire (i.e., the full marks of PEDT questionnaire is 100%).

As can be seen from FIGS. 11, 12, 19 and 20, during the three-month testing of wearing the far-infrared underpants of the present invention, the scores of the subjects were generally lowered, no matter whether the subject was diagnosed with male sexual dysfunction or not. That is, the far-infrared underpants of the present invention can improve the ability of controlling ejaculation.

5.4.3.6. Evaluation of Lower Urinary Tract Symptom (LUTS)

In this test, the effect of far-infrared underpants of the present invention in improving the lower urinary tract symptoms for subjects diagnosed or not diagnosed with male sexual dysfunction during three-month test was evaluated by the following questionnaires: the International Prostate Symptom Score (IPSS, as shown in FIG. 6). The lower the score of the questionnaire the milder the lower urinary tract symptom.

Figure 13:
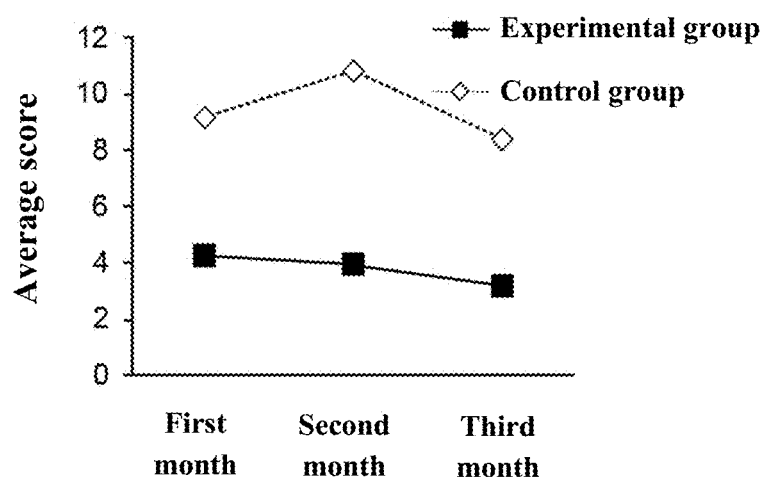
Figure 14:
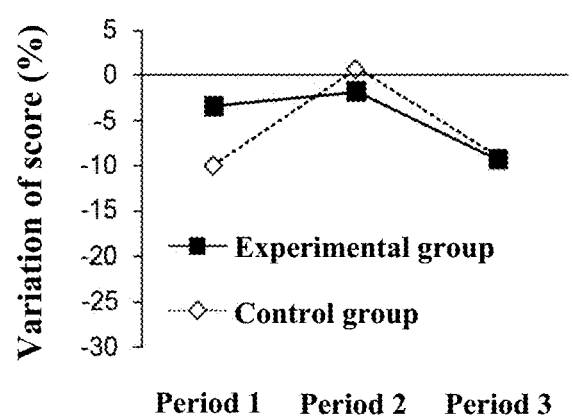
Figure 21:
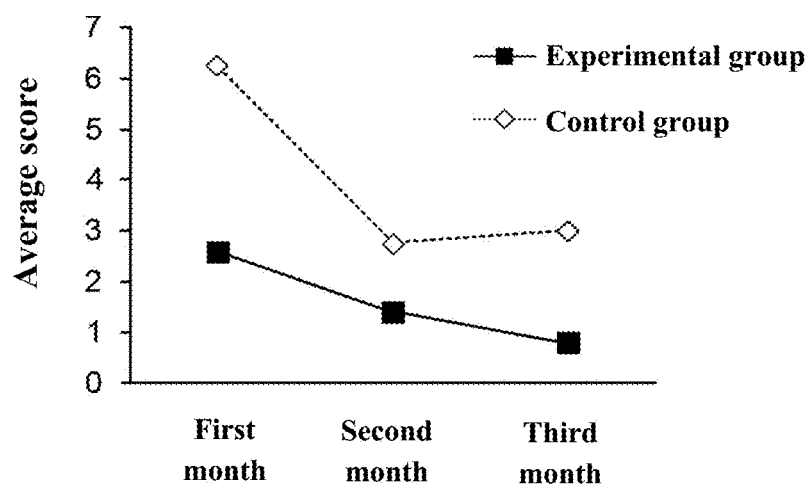
Figure 22:
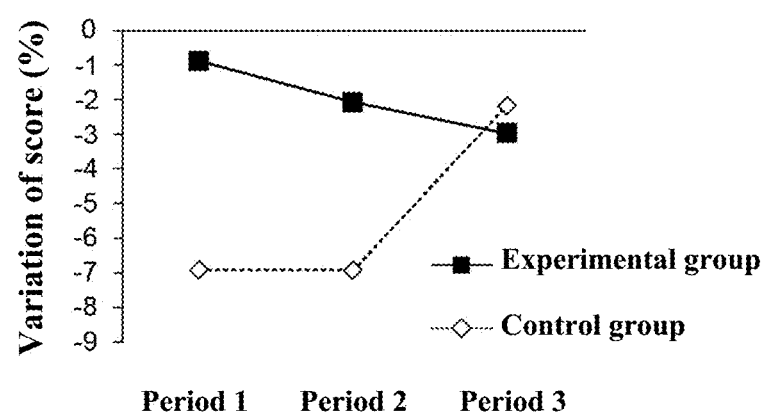

FIGS. 13 and 21 show the average scores of IPSS for subjects diagnosed or not diagnosed with male sexual dysfunction every month during the test, respectively. FIGS. 14 and 22 show the variation in score percentage between two different months, wherein the score percentage was converted from the scores of control group or experimental group based on the full marks of IPSS questionnaire (i.e., the full marks of IPSS questionnaire is 100%).

As can be seen from FIGS. 13, 14, 21 and 22, during the three-month testing of wearing the far-infrared underpants of the present invention, the scores of the subjects were generally lowered, no matter whether the subject was diagnosed with male sexual dysfunction or not. That is, the far-infrared underpants of the present invention can improve lower urinary tract symptoms.

The above example is used to illustrate the principle and efficacy of the present invention and show the inventive features thereof. People skilled in this field may proceed with a variety of modifications and replacements based on the disclosures and suggestions of the invention as described without departing from the principle and spirit thereof. Therefore, the scope of protection of the present invention is that as defined in the claims as appended.

What is claimed is:

1. A masterbatch for manufacturing far-infrared fibers, comprising:
   a first polymer matrix, which is selected from the following group: polyester, polyurethane (PU), poly(vinyl chloride) (PVC), poly propylene (PP), polyamide (PA), and polyethylenimine (PEI); and
   a first far-infrared filler dispersed in the first polymer matrix,
   wherein the first far-infrared filler contains titanium (Ti), germanium (Ge), zinc (Zn), aluminum (Al), magnesium (Mg), silicon (Si), copper (Cu), calcium (Ca), iron (Fe), barium (Ba), potassium (K), and sodium (Na) and wherein the first far-infrared filler does not contain any of scandium (Sc), vanadium (V), chromium (Cr), cobalt (Co), and antimony (Sb),
   wherein based on the total weight of the masterbatch, the amount of titanium ranges from 5 wt % to 40 wt %, the amount of germanium ranges from 0.05 wt % to 0.5 wt %, the amount of zinc ranges from 1 wt % to 12 wt %, the amount of aluminum ranges from 3 wt % to 16 wt %, the amount of magnesium ranges from 1 wt % to 15 wt %, and the amount of silicon ranges from 12 wt % to 22 wt %.

2. The masterbatch of claim 1, wherein the first far-infrared filler further contains one or more of the elements selected from the following group: manganese (Mn), nickel (Ni), and gallium (Ga).

3. A far-infrared fiber, which is manufactured by using the masterbatch of claim 1 and a second polymer.

4. The far-infrared fiber of claim 3, wherein the second polymer is selected from the following group: polyester, polyurethane, poly(vinyl chloride), poly propylene, polyamide, and silicone.

5. The far-infrared fiber of claim 3, wherein the far-infrared fiber is a core-shell fiber, which has a core layer and a shell layer coating the core layer along the long-axis direction of the far-infrared fiber, and wherein the core layer is manufactured by using the masterbatch and the second polymer and the shell layer is formed by a third polymer.

6. The far-infrared fiber of claim 5, wherein the shell layer of the far-infrared fiber further contains a second far-infrared filler dispersed in the third polymer, and the second far-infrared filler contains titanium, germanium, zinc, aluminum, and magnesium, and the second far-infrared filler does not contain any of scandium, vanadium, chromium, cobalt, and antimony.

7. The far-infrared fiber of claim 5, wherein the third polymer is selected from the following group: polyester, polyurethane, poly(vinyl chloride), poly propylene, polyamide, and silicone.

8. The far-infrared fiber of claim 7, wherein the third polymer is silicone.

9. The far-infrared fiber of claim 3, which is a hollow fiber.

10. The far-infrared fiber of claim 5, which is a hollow fiber.

11. A product of far-infrared fibers, which is manufactured by the far-infrared fiber of claim 3 and other optional fibers.

12. The product of claim 11, which further comprises metal granules adhered to the surface of the far-infrared fiber, wherein the metal granules are the granules of one or more metals selected from the following group: gold (Au) and platinum (Pt).

13. The product of claim 11, which is underpants.

14. The product of claim 13, wherein the proportion of the far-infrared fibers in the part of the underpants that corresponds to the front side of a user's pelvis is 40% or more based on the total number of the far-infrared fibers and other optional fibers in that part.

* * * * *